(12) United States Patent
Crumpton

(10) Patent No.: US 8,539,846 B2
(45) Date of Patent: Sep. 24, 2013

(54) SAMPLE RETRIEVAL APPARATUS AND METHOD

(75) Inventor: Eric Crumpton, Lynnwood, WA (US)

(73) Assignee: Global Diving & Salvage, Inc., Seattle, WA (US)

( * ) Notice: Subject to any disclaimer, the term of this patent is extended or adjusted under 35 U.S.C. 154(b) by 130 days.

(21) Appl. No.: 13/275,036

(22) Filed: Oct. 17, 2011

(65) Prior Publication Data
US 2013/0091964 A1     Apr. 18, 2013

(51) Int. Cl.
*G01N 1/00*     (2006.01)

(52) U.S. Cl.
USPC ..................................... 73/863.85

(58) Field of Classification Search
None
See application file for complete search history.

(56) References Cited

U.S. PATENT DOCUMENTS

| | | | | |
|---|---|---|---|---|
| 3,983,904 A | * | 10/1976 | Laviano | 138/89 |
| 4,504,005 A | * | 3/1985 | Moore | 226/190 |
| 5,131,283 A | * | 7/1992 | Canfield | 73/864.74 |
| 5,735,425 A | * | 4/1998 | Beadle | 220/235 |
| 5,823,222 A | * | 10/1998 | Minshull et al. | 137/15.15 |
| 6,293,163 B1 | * | 9/2001 | Johnston et al. | 73/864.74 |
| 6,662,490 B1 | * | 12/2003 | Aesch, Jr. | 43/124 |
| 6,948,391 B2 | * | 9/2005 | Brassell et al. | 73/863.84 |
| 7,930,947 B2 | * | 4/2011 | Counts | 73/863.85 |
| 2004/0056039 A1 | * | 3/2004 | Sarajian | 220/801 |

* cited by examiner

*Primary Examiner* — Robert R Raevis
(74) *Attorney, Agent, or Firm* — Seed IP Law Group PLLC

(57) ABSTRACT

Sample or specimen retrieval may be performed via a tool that includes a multi-section tool bit which carries a plug. A cutter of the tool bit forms (e.g., drill, mill, bore, ream) a hole in a structure. A mandrel on a leading section of the tool bit sealing engages the plug in the hole from a blindside of the structure. A sample chamber of a trailing section of the tool bit extends into the hole through a passage in the plug and is opened. Optionally an auger portion of the trailing section rotates to acquire the sample in the sample chamber. The sample chamber is closed and withdrawn from hole and the mandrel seats in the passage to seal the plug. The trailing section is separated from the leading section, and retrieved along with the sample. Such may be particularly suitable for use with submersible ROVs.

31 Claims, 15 Drawing Sheets

SAMPLE RETRIEVAL APPARATUS AND METHOD

BACKGROUND

1. Field

This application generally relates to sample or specimen retrieval, and particularly to apparatus and methods to retrieve a sample or specimen from within a structure, for instance retrieving a sample of a fluid contained within a hull or a tank using remotely operated vehicles (ROVs).

2. Description of the Related Art

There are many situations where it may be useful to ascertain the contents of a structure. For instance, it may be useful to determine whether a structure such as a vessel, hull, tank or reservoir contains a material. For example, it may be useful to determine whether a structure contains a fluid, and if so it may be useful to determine the location of the fluid, the type of fluid and/or some other physical characteristic of the fluid.

There are a variety of environments were samples or specimens (used interchangeably herein) must be retrieved from structures. Some environments provide easy physical access to one attempting to collect the sample or specimen. For instance, physical access to an above ground structure is typically easy to achieve. Other environments make physical access difficult. For example, underwater structures such as sunken ships, drilling platforms, wells heads, containment vessels, and/or pipes may be difficult to access, particularly when in relatively deep waters. Also for example, underground structures such as underground tanks may also be difficult to access. As a further example, even some above ground structures may be difficult to access, for instance structures which contain or which might contain radioactive materials.

In many instances, remotely operated vehicles (ROVs) are used to gain physical access to these structures. Access via ROVs can be difficult, time consuming, and expensive. Such places a premium on efficiency operation. Such also requires dependable operation since the costs in time and money or repeating an operation is so high. Further, there may be serious adverse consequences if an operation is not correctly performed the first time. For instance, a fluid may leak from a structure if not properly sealed or salvaged.

New systems, methods and apparatus that allow retrieval of samples or specimens are desirable.

BRIEF SUMMARY

This application generally relates to sample or specimen retrieval, and particularly to apparatus and methods to form (e.g., drill, mill, ream, bore) a hole in a structure, retrieve a sample or specimen from within the structure, and seal the hole in the structure. Such may, for instance, be used to retrieve samples from difficult to access structures such structure underwater (e.g., sunken ships), as well as to retrieve samples from easy to access structures. Such may also be particularly suitable for use with ROVs.

A sample retrieval tool to form a hole in a workpiece, retrieve samples from an interior of the workpiece and to perform a blind side expansion to seal the hole in the workpiece, may be summarized as including a plug comprising a head and a body, a flange bearing surface formed by a transition between the head and the body to bear against an exterior surface of the workpiece, a passage extending through the head and the body, the body being plastically expandable between an unexpaded configuration in which a portion of the body is sized to be receivable through the hole in the workpiece and an expanded configuration in which at least some of the portion of the body is sized to be in sealing engagement with at least a portion of the workpiece; and a multi-section tool bit comprising a leading section and a trailing section selectively detachable from the leading section, the leading section comprising an elongated stem having a front end and a rear end, a cutter at least proximate at least the front end of the stem, a mandrel section spaced rearwardly from the cutter, the mandrel section having an outer perimeter sized to be received in a portion of the passage that extends through the body of the plug and to plastically expand at least a portion of the body of the plug into the expanded configuration as the mandrel section is moved rearwardly through the portion of the passage from a blindside of the hole in the workpiece, the trailing section comprising an elongated shank having a leading end, a trailing end, and a sample chamber that is openable to receive a sample therein and closable to retain the sample therein.

The trailing section of the tool bit may include an auger portion. The sample chamber may be formed by a sleeve that surrounds a portion of trailing section of the tool bit.

The sleeve may be selectively displaceable from a closed position in which the sample chamber is open to receive the sample to a closed position in which the sample chamber is closed to retain the sample therein. The trailing section of the tool bit may include a spring that biases the sleeve toward the closed position. The trailing section of the tool bit may include a sleeve stop extending radially from the shank of the trailing section and the trailing section may also include a spring that biases the sleeve forwardly toward the closed position in which a portion of the sleeve engages the sleeve stop.

The stem of the leading section of the tool bit may have an externally threaded portion rearward of the cutter, the body and the head of the plug may be a unitary piece of a plastic material, and the plug may further include a metal nut received in the passage in the head and having a threaded passage sized to threadedly receive the externally threaded portion of the leading section of the tool bit. The passage may be longitudinal, the body may have a number of longitudinally extending flutes formed therein and a number of seals thereabout, and the metal nut may be retained in the longitudinal passage in the head by a number of set screws. At least a portion of the passage of the plug may be tapered, having an inner perimeter that decreases in size along a longitudinal axis in a direction towards the head of the plug.

The leading and trailing sections of the tool bit may have a separable portion therebetween that allows the separation of the leading section from the trailing section. The leading section may be attachably and detachably coupled to the trailing section by the separable portion. The separable portion may include a leading section coupler at least proximate the rear end of the stem and the trailing section coupler at least proximate a leading end of the shank that is complimentary to the leading section coupler. The leading section of the tool bit may have an externally threaded portion rearward of the cutter, the leading section coupler may include a threaded female member and the coupler of the trailing section may include a threaded male member threadably engageable with the threaded female member of the leading section, and a thread of the externally threaded portion may be reverse with respect to a thread of the threaded female member.

The leading and trailing sections of the tool bit may have a necked region therebetween, the necked region sized to break to separate the leading section from the trailing section under a defined torque.

The mandrel section may be a tapered mandrel section having an outer perimeter that decreases rearwardly along the tapered mandrel section. The tapered mandrel section may be slidably receivable on the stem, and the leading section may further include a washer received on the stem between the tapered mandrel and the cutter.

The trailing section may have a coupler at least proximate the trailing end; and may further include a drill comprising a motor and a coupler sized and dimension to drivingly couple to the coupler of the trailing section of the tool bit; and a grip selectively operable to engage the head of the plug and to push the body of the plug into the hole in the workpiece.

The trailing section may have a coupler at least proximate the trailing end; and may further include a drill comprising a motor and a coupler sized and dimension to drivingly couple to the coupler of the trailing section of the tool bit; and a grip selectively operable to engage the head of the plug and prevent rotation of the plug in the hole in the workpiece.

A method of operating a sample retrieval tool including a plug and multi-section tool bit to retrieve a sample from an interior of a workpiece may be summarized as including forming a hole in the workpiece from one side through to a blindside of the workpiece with the multi-section tool bit while the tool bit carries the plug; advancing the plug into the formed hole to position a portion of a body of the plug in the blind side of the workpiece; withdrawing the tool bit through a passage in the plug to expand at least a portion of the body of the plug from the blind side of the workpiece with a mandrel section of the tool bit to secure the plug in the hole; advancing the tool bit through the passage in the plug to position at least a portion of a sample chamber of the tool bit on the blind side of the workpiece with the sample chamber at least partially open; retracting the tool bit to seat the mandrel section of the tool bit securely in a portion of the passage that extends through at least a portion of the body of the plug; and separating a portion of the tool bit that includes the sample chamber from a portion of the tool bit that includes the mandrel section.

Forming a hole in the workpiece may include rotating the tool bit in a first rotational direction and wherein withdrawing the tool bit through a passage in the plug may include rotating the tool bit in a second rotational direction, opposite the first rotational direction. Advancing the tool bit through the passage in the plug to position at least a portion of a sample chamber of the tool bit on the blind side of the workpiece may include rotating the tool bit in the first rotational direction. Separating a portion of the tool bit that includes the sample chamber from a portion of the tool bit that includes the mandrel section may include rotating the tool bit in the second rotational direction to apply a torque to the tool bit after the mandrel section has securely engaged the plug in the hole in the workpiece.

The method of operating a sample retrieval tool including a plug and multi-section tool bit to retrieve a sample from an interior of a workpiece may further include pulling the tool bit rearwardly to close the sample chamber; and reengaging a thread on the tool bit with a thread of the plug after pulling the tool bit rearwardly and before retracting the tool bit.

The method of operating a sample retrieval tool including a plug and multi-section tool bit to retrieve a sample from an interior of a workpiece may further include rotating the tool bit to auger a viscous fluid into the sample chamber after advancing the tool bit through the passage in the plug to position at least a portion of a sample chamber of the tool bit on the blind side of the workpiece and before retracting the tool bit.

Withdrawing the tool bit through a passage in the plug to expand at least a portion of the body of the plug from the blind side of the workpiece with a mandrel section of the tool bit to secure the plug in the hole may include withdrawing the tool bit through the passage to expand at least the portion of the body of the plug from the blind side of the workpiece with a tapered mandrel section of the tool bit. Advancing the plug into the formed hole to position a portion of a body of the plug in the blind side of the workpiece may include pushing the plug with a holder.

A plug for use in sample retrieval to seal a hole in a workpiece via a blind side expansion of a portion of the plug while allowing retrieval of a sample from with the workpiece may be summarized as including a unitary piece of a plastic material having a head, a body and a flange bearing surface formed by a transition between the head and the body to bear against an exterior surface of the workpiece, a passage extending through the head and the body, at least a portion of the body being plastically expandable between an unexpanded configuration in which a portion of the body is sized receivable through the hole in the workpiece and an expanded configuration in which at least some of the portion of the body is sized to be in sealing engagement with at least a portion of the workpiece when expanded from the blind side of the workpiece by a mandrel pull through the passage of the plug; and a metal nut that is retained in the passage in the head.

The body may be a cylindrical tube and the passage is longitudinal. The body may have a number of longitudinally extending flutes formed therein.

The plug for use in sample retrieval to seal a hole in a workpiece via a blind side expansion of a portion of the plug while allowing retrieval of a sample from with the workpiece may include at least two O-ring seals received about an exterior of the body and spaced longitudinally along the body with respect to one another.

The plug of for use in sample retrieval to seal a hole in a workpiece via a blind side expansion of a portion of the plug while allowing retrieval of a sample from with the workpiece may include a number of set screws that retain the metal in the passage in the head.

At least a portion of the passage may be tapered, having an inner perimeter that decreases in size along a longitudinal axis in a direction towards the head of the plug.

BRIEF DESCRIPTION OF THE SEVERAL
VIEWS OF THE DRAWING(S)

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings. The various embodiments are illustrated by way of example and not by way of limitation in the accompanying Figures.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with drills, cutters (e.g., drilling, milling, reaming or boring cutters or bits), and/or ROVs have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Figure 1A:
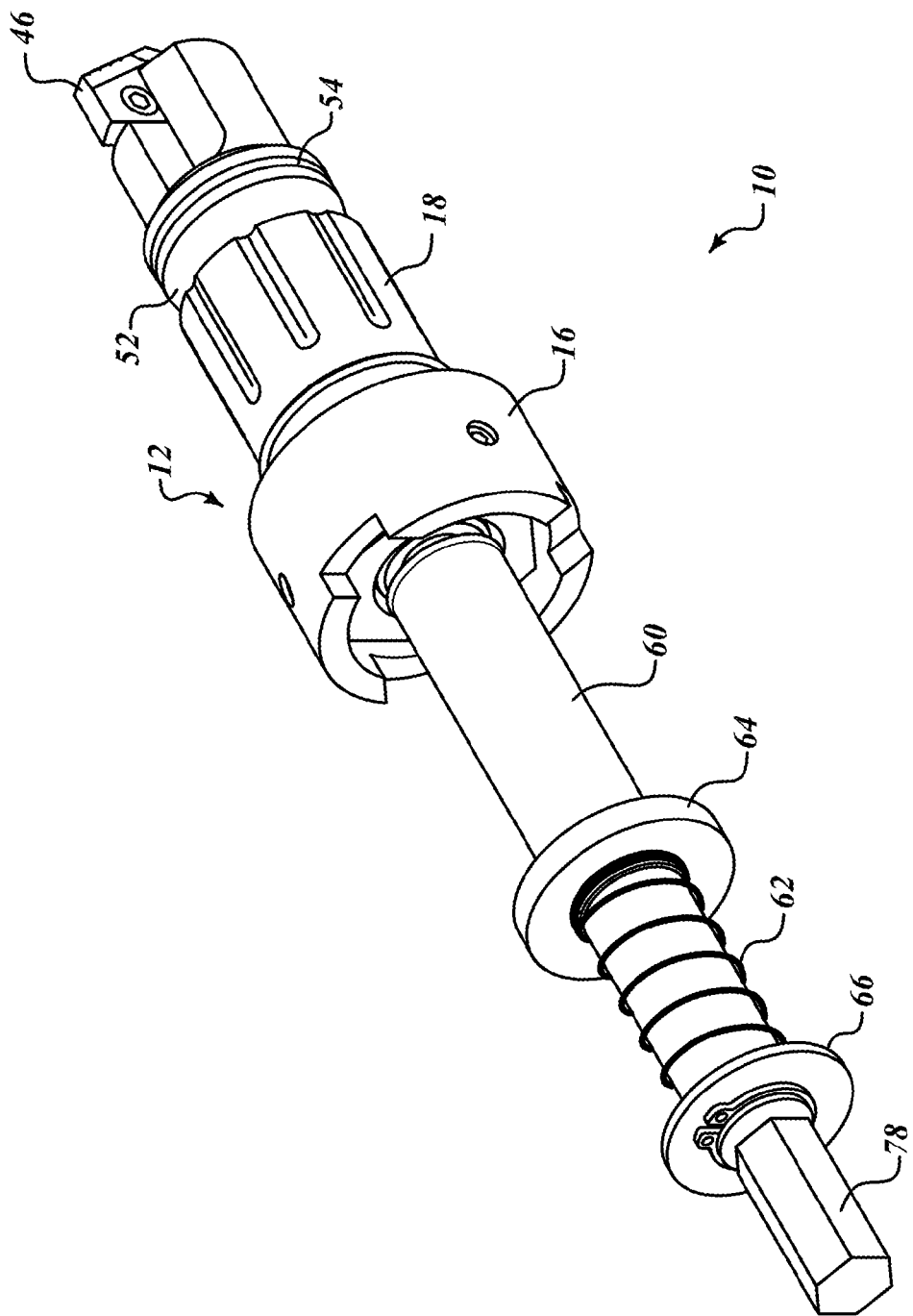
FIG. 1A is an isometric view of a sample retrieval tool to form a hole in a structure, retrieve samples from an interior of the structure, and perform a blind side expansion to seal the hole in the structure, according to one illustrated embodiment, the sample retrieval tool including a plug and a multi-section tool bit including a cutter and a sample chamber.
Figure 1B:
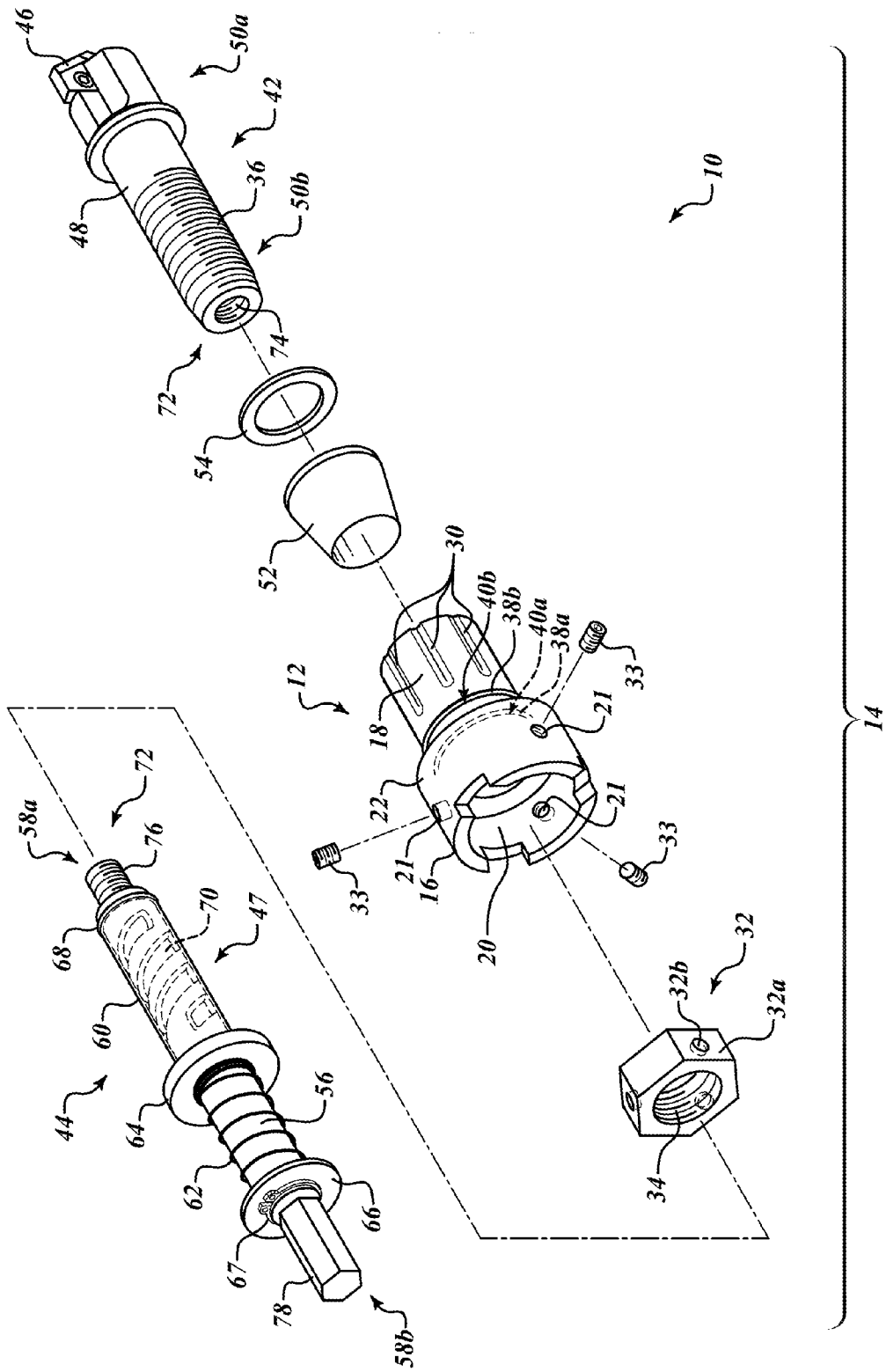
FIG. 1B is an exploded isometric view of the sample retrieval tool of FIG. 1A.
Figure 2:
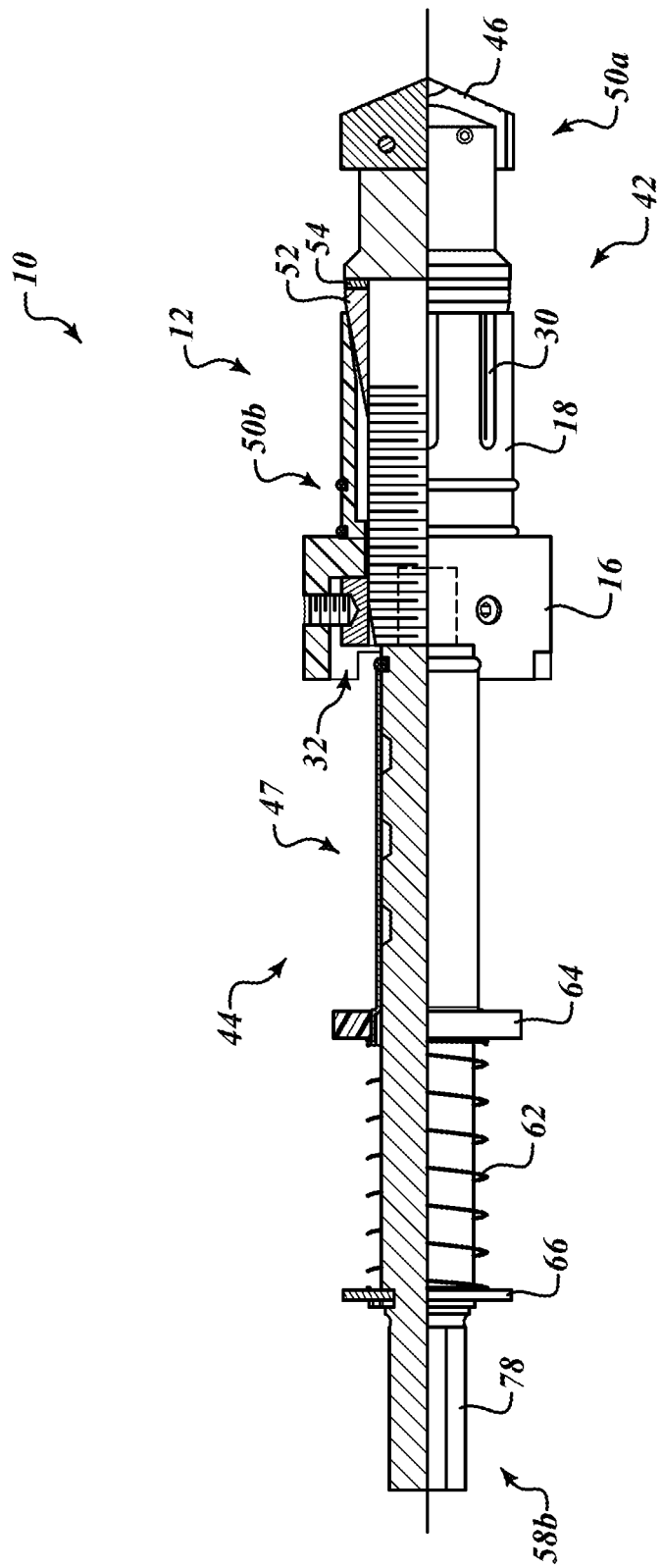
FIG. 2 is a partially sectioned side elevational view of the sample retrieval tool of FIGS. 1A and 1B.

FIGS. 1A, 1B and 2 show a sample retrieval tool 10, according to one illustrated embodiment.

The sample retrieval tool includes a plug 12 and a multi-section tool bit 14, a portion of which carries the plug 12.

The plug 12 includes a head 16 and a body 18, and includes a passage 20 that extends through the head 16 and the body 18. A flange bearing surface 22 is formed by a transition between the head 16 and the body 18. In use the body 18 is received through a hole 24 (FIGS. 5-13) in a structure or workpiece 26 (FIGS. 4-13) and the flange bearing surface 22 bears against an exterior or outer surface 28 of the workpiece 26. At least the body 18 of the plug 12 is plastically expandable between an unexpanded configuration (illustrated in FIGS. 1A, 1B, 2, and 4-7) in which a portion of the body 18 is sized to be receivable through the hole 24 in the workpiece 26 and an expanded configuration (illustrated in FIGS. 8-13) in which at least some of the portion of the body 18 is sized to be in sealing engagement with at least a portion of the workpiece 26. To facilitate expansion, the body 18 may have a number of longitudinally extending slots, flutes or other expansion facilitation structures (e.g., recesses, perforations) 30 formed therein. Additionally, or alternatively, a wall thickness of the body 18 may be selected to allow expansion and plastic deformation with, or without, such expansion facilitating structures 30.

Figure 3A:
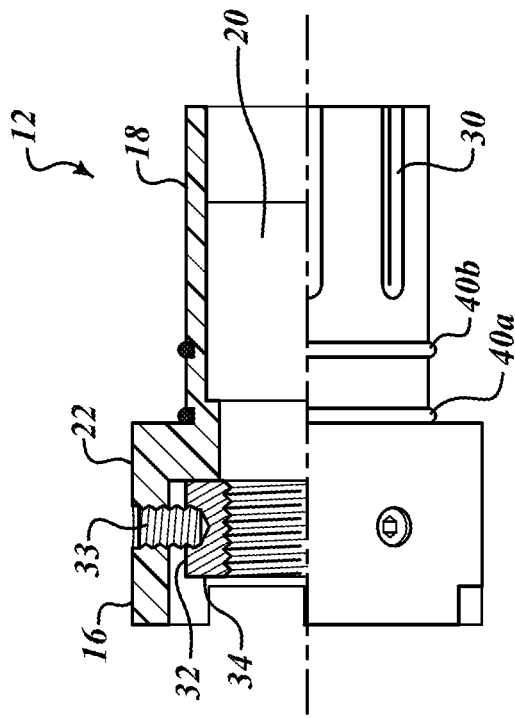
FIG. 3A is a side elevational view of the plug of the sample retrieval tool, according to one illustrated embodiment, including a cylindrical passage.
Figure 3B:
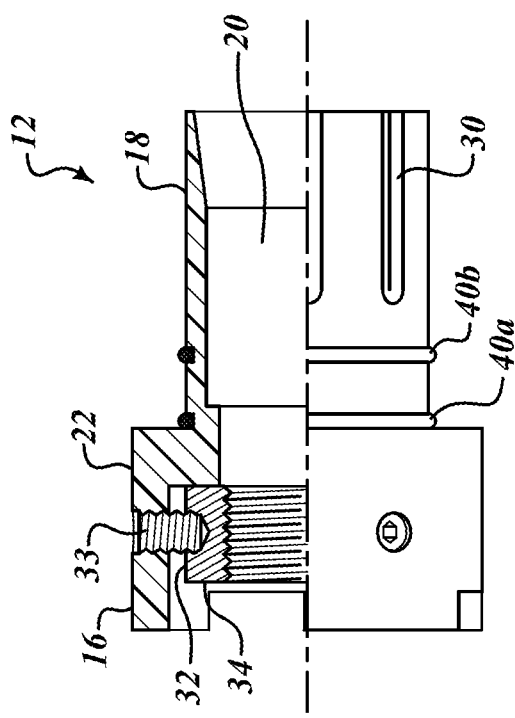
FIG. 3B is a side elevational view of the plug of the sample retrieval tool, according to one illustrated embodiment, including a tapered passage.

The body 18 and the head 16 of the plug 12 may take the form of a unitary piece of a plastic or polymer material (e.g., polyoxymethylene plastic such as Delrin®, Nylon). The plug 12 may be generally cylindrical, the body 18 and optionally the head 16 having a circular outer perimeter. Alternatively, other shapes may be employed, particular where the outer perimeter of the body 18 fits the profile of the hole 24. The passage 20 may be longitudinal and may be coaxial with a center of rotation of the body 18 and head 16. As best illustrated in FIG. 3A, the passage 20 will typically be cylindrical, having a constant diameter through the body 18 of the plug 12, and a constant, although possible different, diameter through the head 16 of the plug 12. Alternatively, as illustrated in FIG. 3B, at least a portion of the passage 20 of the plug 12 may be conical having an inner perimeter that tapers along at least a portion of a longitudinal axis. For example, the inner perimeter may decrease in size along a longitudinal axis in a direction towards the head 16 of the plug 12. The decrease in size may be a linear decrease or nonlinear decrease. The tapered passage 20 may assist with expansion of the plug 12 to the expanded configuration.

The plug 12 may also include a metal nut 32 having a threaded passage 34 to threadedly mate with a complementary thread 36 on an exterior surface the multi-section tool bit 14. The metal nut 32 may be particularly useful where the body 18 and the head 16 of the plug 12 are formed of a plastic material, providing a more robust bearing surface for the threaded engagement between the nut and the multi-section tool bit. The nut 32 may be received in the passage 20 positioned in a portion of the passage 20 extending through the head 16 of the plug 12. Flats 32a (only one called out) of the nut 32 may restrain the nut 32 in the passage 20 against torque or rotation. One or more fasteners, for instance set screws 33, may retain the nut 32 in the passage 20, as well as restrain against torque or rotation.

The body 18 of the plug 12 may optionally include a number seals 38a, 38b (collectively 38) thereabout. The seals 38 may, for example, comprises O-ring seals. The seals 38 may be any suitable material, including rubber, silicon, Teflon, or a relatively soft metal (e.g., cooper, aluminum). The body 18 of the plug 12 may optionally include one or more circumferential recesses 40a, 40b (collectively 40) in which the seals 38 are seated.

The multi-section tool bit 14 includes a leading section 42 and a trailing section 44 which is selectively detachable from the leading section 42. The leading section 42 carriers the plug 12, and includes a cutter 46 to form (e.g., drill, mill, bore, ream) a hole 24 in a workpiece 26. The trailing section 44 includes a sample chamber 47.

The leading section 42 includes an elongated stem 48 having a front end 50a and a rear end 50b. The cutter 46 is at least proximate at least the front end of the stem 48. The leading section 42 includes a mandrel section 52 spaced rearwardly from the cutter 46. The mandrel section 52 has an outer perimeter sized to be received in a portion of the passage 20 that extends through the body 18 of the plug 12 and to plastically expand at least a portion of the body 18 of the plug 12 into the expanded configuration as the mandrel section 52 is moved rearwardly through the portion of the passage 20 from a blind side of the hole 24 in the workpiece 26. For example, the mandrel section 52 may be a tapered mandrel section 52 (as illustrated in FIGS. 1A, 1B and 2) having an outer perimeter that decreases rearwardly along the tapered mandrel section 52. Alternatively, the mandrel section 52 may not be tapered, but rather may interface with a tapered passage 20 (FIG. 3B) of the plug 12 to achieve the desired expansion of the body 18 of the plug 12. Notably, a tapered mandrel section 52 may also be used with the tapered passage 20 (FIG. 3B).

The tapered mandrel section 52 may be slidably receivable on the stem 48. This may advantageously reduce the cost of manufacture. This may also allow tapered mandrels of various sizes to be interchangeably used with a single size stem 48, to accommodate different plug 12 sizes. Alternatively, the tapered mandrel section 52 may be machined or otherwise integrally formed on the elongated stem 48. Where the tapered mandrel section 52 is slidably received on the stem 48, the leading section 42 may further include a washer 54 received on the stem 48 between the tapered mandrel section 52 and the cutter 46.

The stem 48 of the leading section 42 of the multi-section tool bit 14 may include the externally threaded portion 36 spaced rearward of the cutter 46 to complementarily threadedly engage the threaded passage 34 of the nut 32 of the plug 12. Notably, this threaded engagement is selectively detachable and attachable. Thus, the leading section 42 may selectively and/or successively engage, disengage and reengage the plug 12.

The trailing section 44 includes an elongated shank 56 having a leading end 58a, a trailing end 58b. The sample chamber 47 is openable to receive a sample therein and closable to retain the sample therein. The sample chamber 47 may be formed by a cover or sleeve 60 that surrounds a portion of the shank 56 of the trailing section 44 of the multi-section tool bit 14. The cover or sleeve 60 is selectively displaceable from a closed position (FIGS. 1A, 2, 5-9) to an open position (FIG. 10) in which the sample chamber 47 is open to receive the sample and back to the closed position (FIGS. 11-13) in which the sample chamber 47 is closed to retain the sample therein. For example, the trailing section 44 of the multi-section tool bit 14 may include a biasing member, for instance a spring such as a coil compression spring 62, that biases the cover or sleeve 60 toward the closed position. The compression spring 62 may be positioned between a flange 64 at a rear of the cover or sleeve 60 and a rear flange or stop 66 fixed to the trailing section 44. The rear flange or stop 66 fixed to the trailing section 44 may be fixed via a removable fasteners, for instance a clip 67. The trailing section 44 of the multi-section tool bit 14 may also include a sleeve stop 68 that extends radially from the shank 56 of the trailing section 44. The spring 62 may bias the cover or sleeve 60 forwardly toward the closed position in which a portion of the cover or sleeve 60 engages the sleeve stop 68. A removable fastener such as the clip 67 may permit the position of the rear flange or stop 66 to be modified to accommodate various thicknesses of workpieces 26.

The trailing section 44 of the multi-section tool bit 14 may also advantageously include an auger portion 70. The auger portion 70 may be particular useful to obtain samples of viscous or highly viscous fluids. For example, oil at low temperatures commonly found in deep water.

As previously noted, the leading section 42 and trailing section 44 of the multi-section tool bit 14 have a separable portion 72 therebetween that allows the separation of the leading section 42 from the trailing section 44. To accomplish such the leading section 42 may be attachably and detachably coupled to the trailing section 44 by the separable portion. For example, the separable portion 72 may include a leading section coupler 74 at least proximate the rear end 50b of the stem 48 and the trailing section coupler 76 at least proximate the leading end 58a of the shank 56 that is complimentary to the leading section 42 coupler. As illustrated, the leading section coupler 74 may include a threaded female member and the trailing section coupler 76 may include a threaded male member, sized and dimensioned to be threadably engageable with the threaded female member of the leading section coupler 74. The thread of the externally threaded portion 36 may be reverse or opposite the thread of the threaded female member. Alternatively, the leading section coupler 74 may include a threaded male member and the trailing section coupler 76 may include a threaded female member, sized and dimensioned to be threadably engageable with the threaded male member of the leading section coupler 74. As a further alternative, the leading and trailing sections 42, 44 of the multi-section tool bit 14 may have a necked region therebetween, the necked region sized to break to separate the leading section 42 from the trailing section 44 under a defined torque.

The trailing section 44 may have a coupler 78 at least proximate the trailing end 58b to allow the multi-section tool bit 14 10 to be coupled to a drive mechanism or transmission of a drive mechanism. For example, the coupler 78 may take the form of hexagonal facets or flats formed about a periphery of the trailing end 58b be engaged by a chuck of a machine 80 (FIG. 4).

Figure 4:
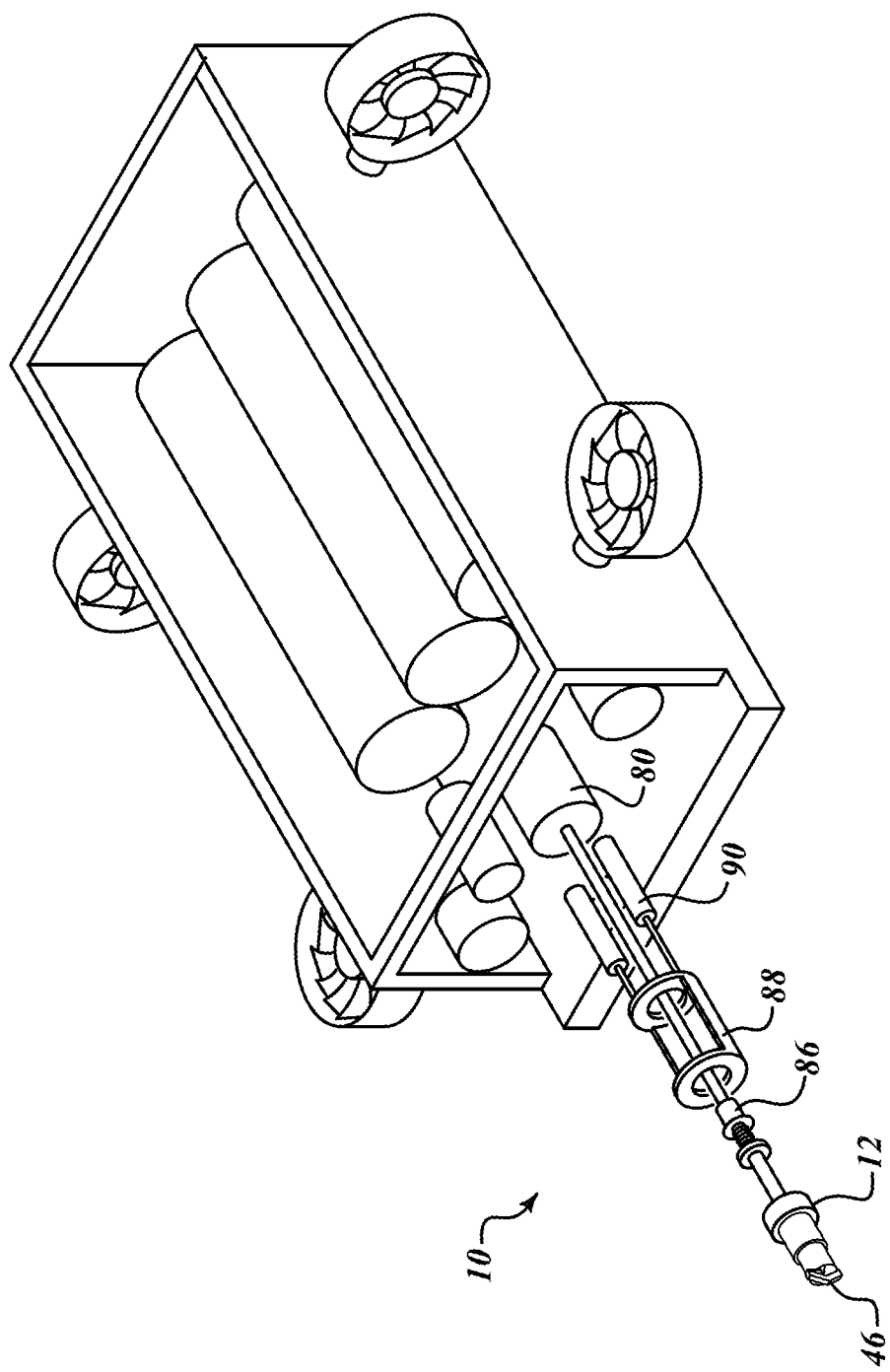
FIG. 4 is an isometric view of a submersible remotely operated vehicle carrying a sample retrieval tool including a plug, multi-section tool bit, machine and holder or gripper, according to one illustrated embodiment.

FIG. 4 shows a submersible ROV 82 carrying a sample retrieval tool 10, according to one illustrated embodiment.

While the sample retrieval tool 10 may include only the plug 12 and multi-section tool bit 14, in some embodiments the sample retrieval tool 10 may further include the machine 80 comprising a motor 84, a coupler 86 sized and dimension to drivingly couple to the coupler 78 (FIGS. 1A, 1B and 2) of the trailing section 44 of the multi-section tool bit 14, and optionally a transmission (e.g., gears). The machine 80 may take a variety of forms such as a drill, miller, borer or reamer. The machine 80 may be mounted on a vehicle, for example the submersible ROV 82. Alternatively, the multi-section tool bit 14 including the machine 80 may be handheld. Also as illustrated in FIG. 4, the sample retrieval tool 10 may further include a grip or holder 88 selectively operable to engage the head 16 of the plug 12 and prevent rotation of the plug 12 in the hole 24 in the workpiece 26. The gripper or holder 88 may additionally or alternatively be operable to engage the head 16 of the plug 12 and to push the body 18 of the plug 12 into the hole 24 in the workpiece 26. The grip or holder 88 may be operated via one or more pistons 90, or any other actuation capable of moving the gripper or holder 88.

FIGS. 5-13 show the operation of the sample retrieval tool 10 with respect to the workpiece at successive intervals, and are discussed below. Show operation is further set out in the flow diagram of FIG. 14, also discussed below.

Figure 5:
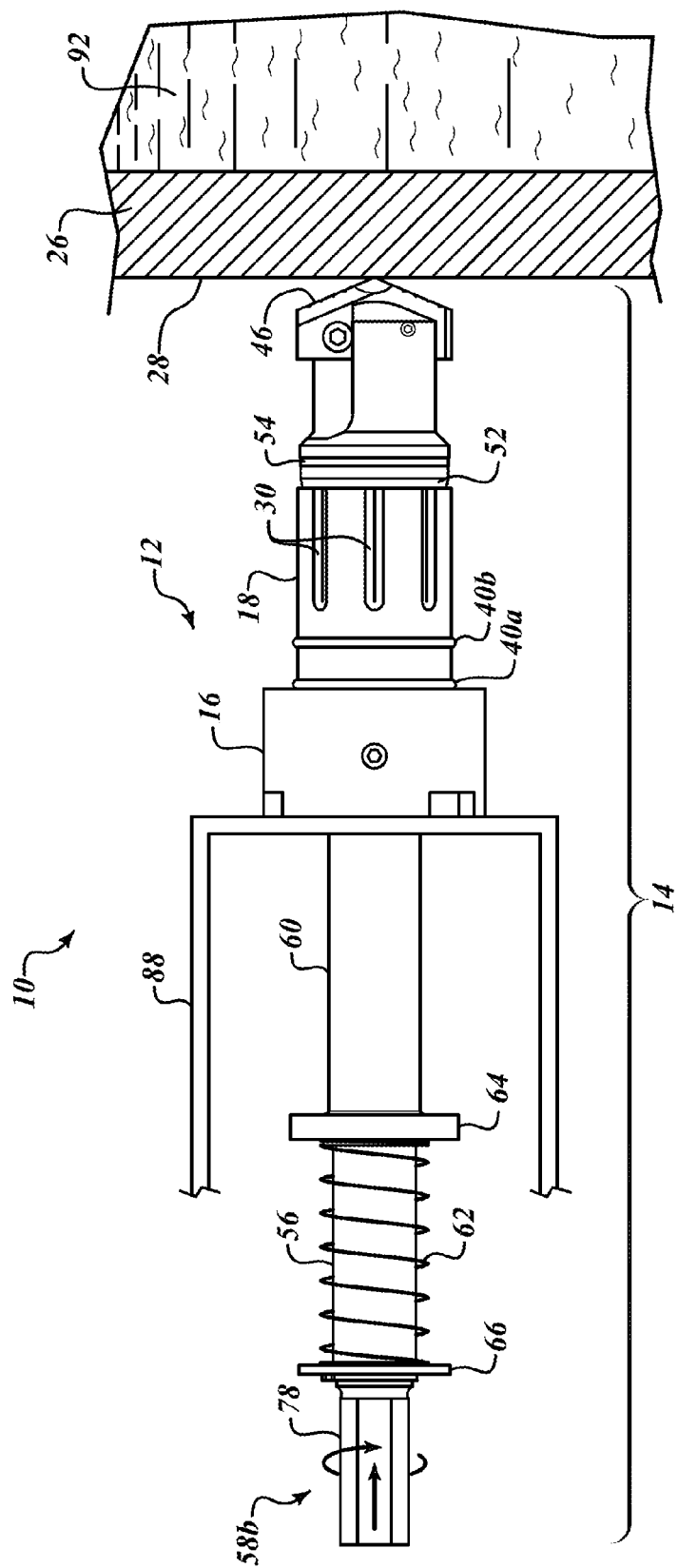
FIG. 5 is a side elevational view of the sample retrieval tool positioned to form a hole in a structure or workpiece, according to one illustrated embodiment.

FIG. 5 shows the sample retrieval tool 10 positioned at a start of a sample retrieval process with the cutter 46 positioned on a workpiece 26 from which a sample or specimen will be withdrawn or retrieved. The machine 80 (FIG. 4) turns in a first rotational direction (e.g., clockwise), rotating the multi-section tool bit 14 and the cutter 46 to form a hole 24 through the workpiece 26 to access an interior or a blind side of the workpiece 26. The workpiece 26 may be a structure, for example a vessel, hull or tank, which may have an interior in which a material 92, for instance a fluid, may possible reside. The sample retrieval tool 10 may be used to determine whether a material 92 resides in the interior of the workpiece 26, and/or the type of material 92.

Figure 6:
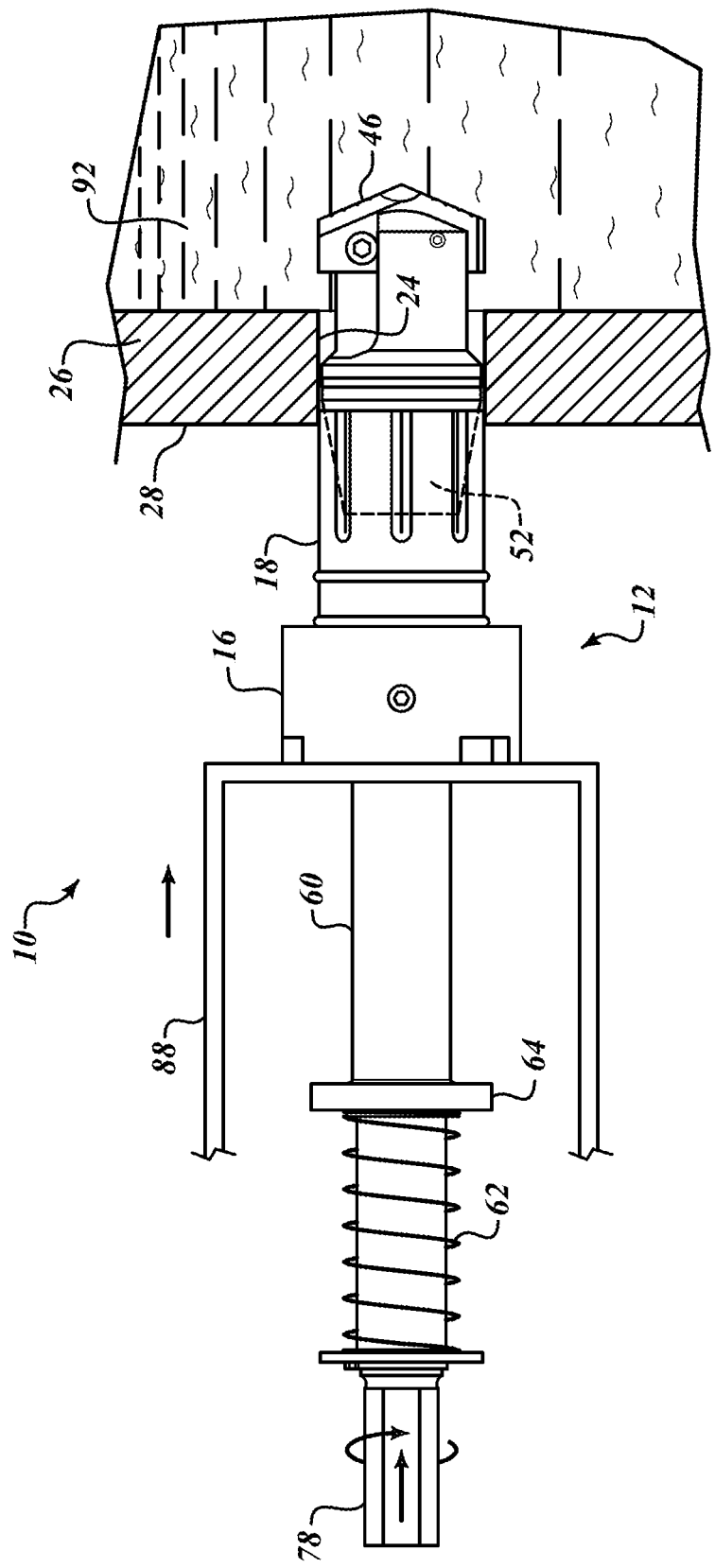
FIG. 6 is a side elevational view of the sample retrieval tool showing the cutter extending through the hole to a blind side of the structure or workpiece, according to one illustrated embodiment.

FIG. 6 shows the sample retrieval tool 10 with the cutter 46 protruding through the workpiece 26 and the plug 12 positioned to be inserted into the workpiece 26. Notably, the plug 12 is in the unexpanded configuration. The body 18 of the plug 12 may be sized and dimensioned to be closely received in the hole 24 formed by the cutter 46 when the plug 12 is in the unexpanded configuration. The head 16 of the plug 12 may be sized larger than the hole 24 to provide the flange bearing surface 22. As illustrated in FIG. 6, the gripper or holder 88 may be positioned to engage the head 16 of the plug 12 and used to insert the plug 12 into the hole 24. Alternatively, the plug 12 may be carried into the hole 24 by the multi-section tool bit 14.

Figure 7:
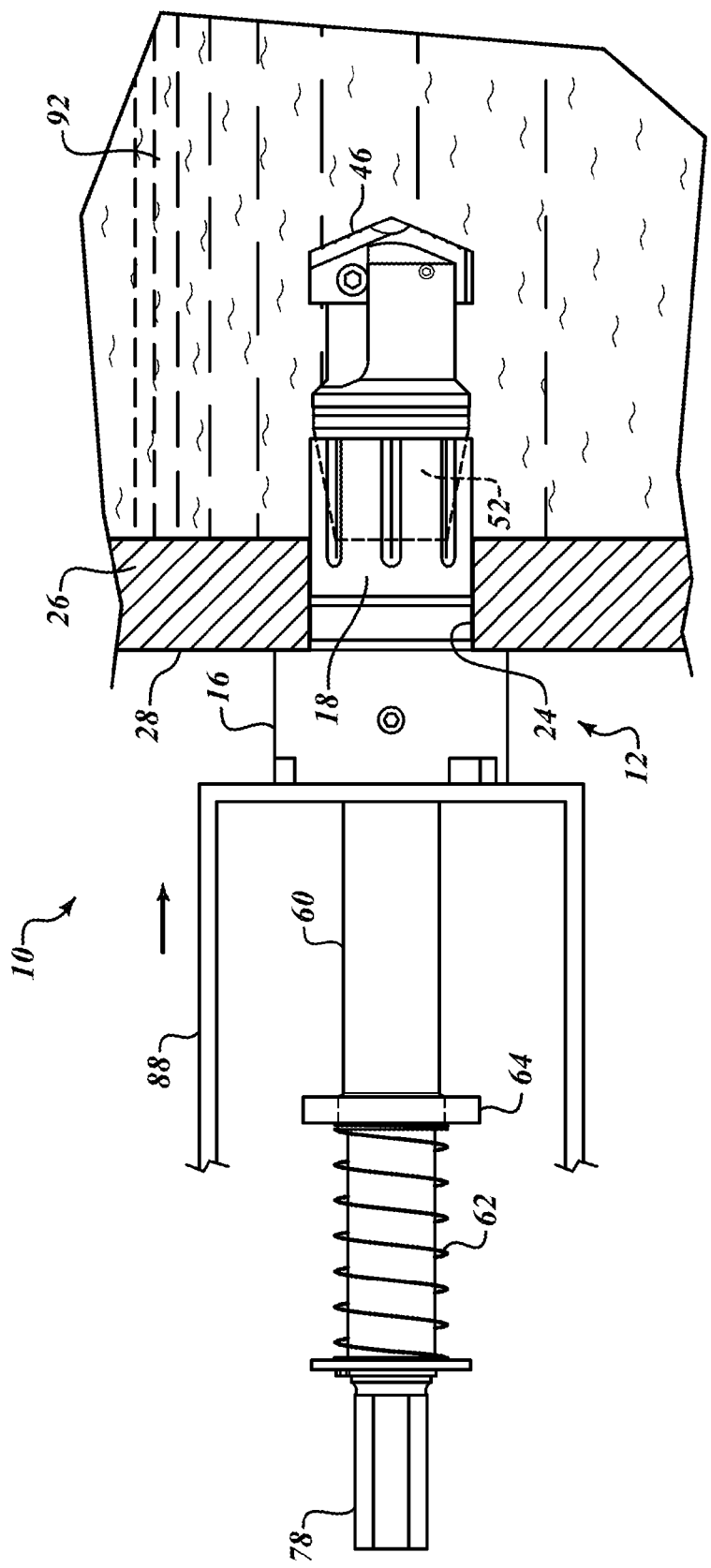
FIG. 7 is a side elevational view of the sample retrieval tool showing the body of the plug extending through and protruding from the hole, in an unexpanded configuration, according to one illustrated embodiment.

FIG. 7 shows the sample retrieval tool with the body 18 of the plug 12 inserted into the hole 24 formed by the cutter 46, a portion of the body 18 extending beyond a blind side 94 of the workpiece 26. The flange bearing surface 22 of the plug 12 is adjacent to an outer surface 96 of the workpiece 26. Notably, the body 18 of the plug 12 is still in the unexpanded configuration.

Figure 8:
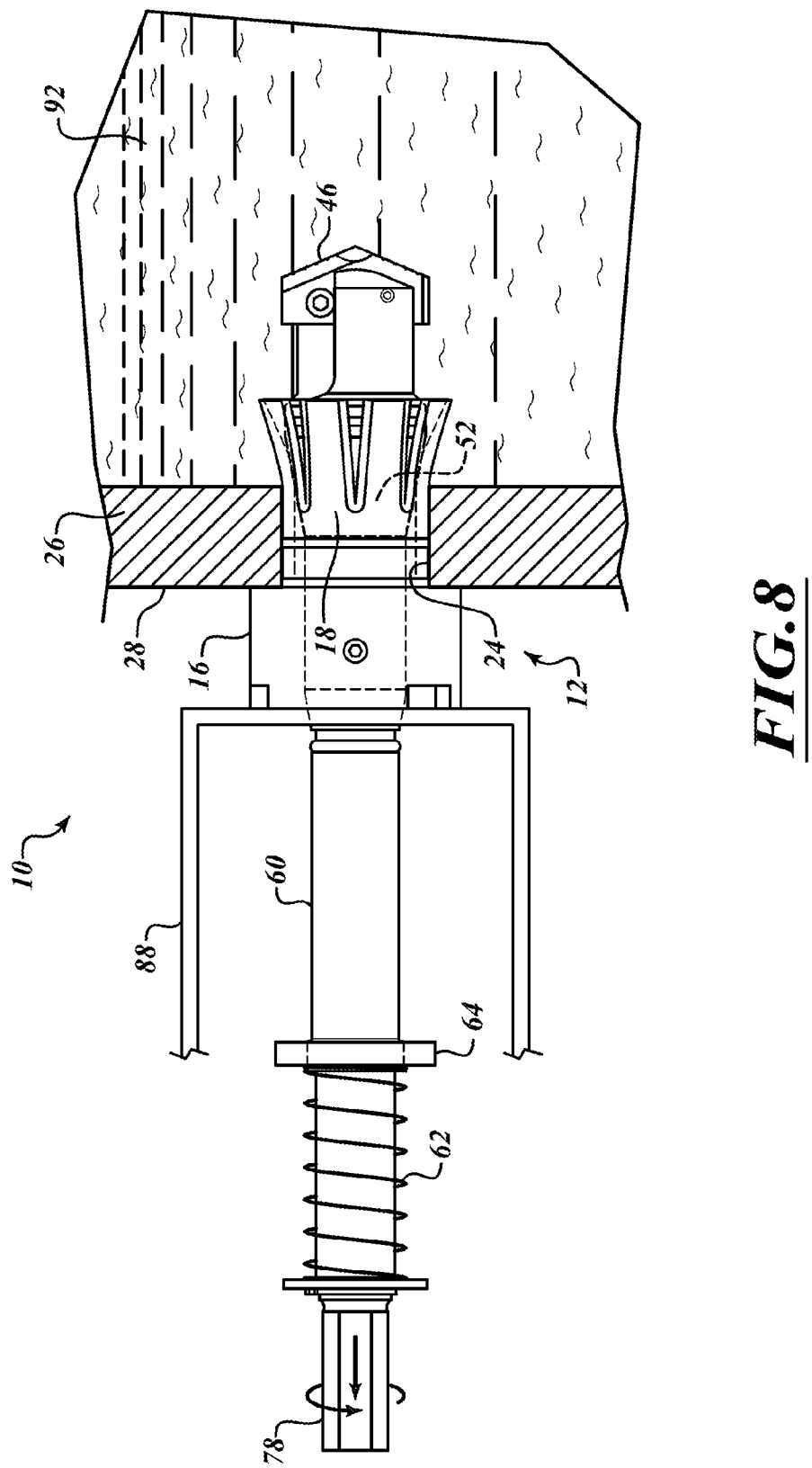
FIG. 8 is a side elevational view of the sample retrieval tool showing a mandrel section of the multi-section tool bit withdrawn rearwardly to expand at least a portion of the body of the plug into a sealing engagement with the structure or workpiece, according to one illustrated embodiment.

FIG. 8 shows the sample retrieval tool 10 with the body 18 of the plug 12 expanded into the expanded configuration to sealing engage at least a portion of the workpiece 26. The plug 12 is expanded by rearward (i.e., back in direction opposite the direction of travel during the drilling, milling, boring, reaming or machining from the interior to the exterior of the workpiece 26) movement of the mandrel section 52 of the leading section 42 of the multi-section tool bit 14. In particular, such rearward movement may be obtained by rotating the shank 56 and stem 48 by the machine 80, for example in a second rotational direction (e.g., counterclockwise), opposite the first rotational direction. Such may cause the externally threaded portion 36 on the leading section 42 to withdraw through the threaded passage 34 of the nut 32 in the plug 12, providing relative translational movement therebetween. While the plug 12 is retained against rearward translation by the workpiece 26 as the mandrel section 52 moves rearwardly along with the leading section 42 with respect to the plug 12, the taper of the mandrel section 52, or alternatively or additionally the taper of the passage 20 (FIG. 3B) of the plug 12, causes a least a portion of the body 18 of the plug 12 to expand radially outward. Optionally, the holder or gripper 88 may restrain the plug 12 from rotating in the hole 24 along with the multi-section tool bit 14 with respect to the workpiece 26.

Figure 9:
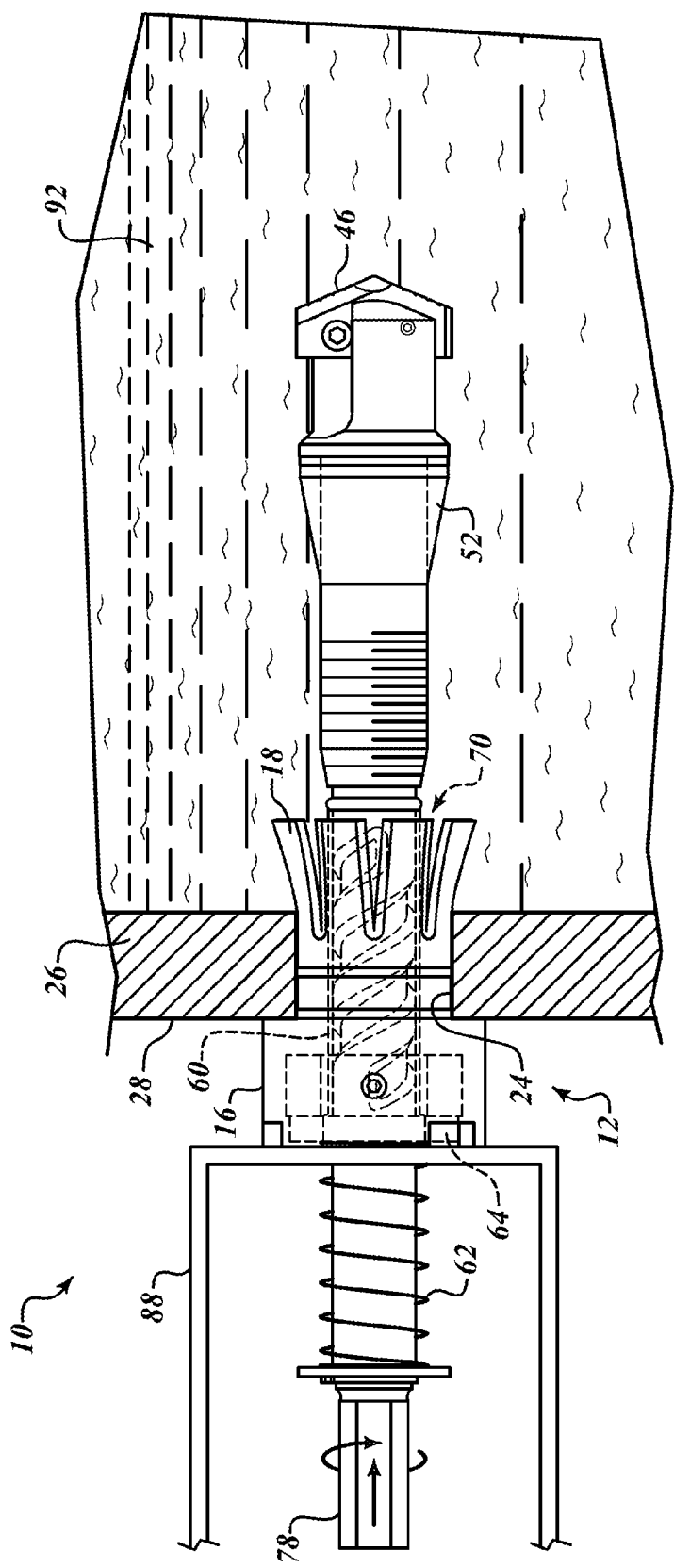
FIG. 9 is a side elevational view of the sample retrieval tool showing the multi-section tool bit moved forwardly to extend into an interior of the structure or workpiece, according to one illustrated embodiment.

FIG. 9 shows the sample retrieval tool 10 with the multi-section tool bit 14 moved forwardly with respect to the plug 12 and workpiece 26 to expose the sample chamber 47 to the interior or blind side 94 of the workpiece 26. In particular, a force may be applied by the machine 80 or gripper or holder 88 to translate the multi-section tool bit 14 inwardly into the structure or workpiece 26. The plug 12 is fixed in the workpiece 26 so does not translate along with the multi-section tool bit 14. The flange 64 of the cover or sleeve 60 of the sample chamber 47 may engage a portion of the plug 12, pushing the cover or sleeve 60 rearwardly against the biasing force of the compression spring 62 toward the rear flange or stop 66, opening or exposing an interior of the sample chamber 47.

Figure 10:
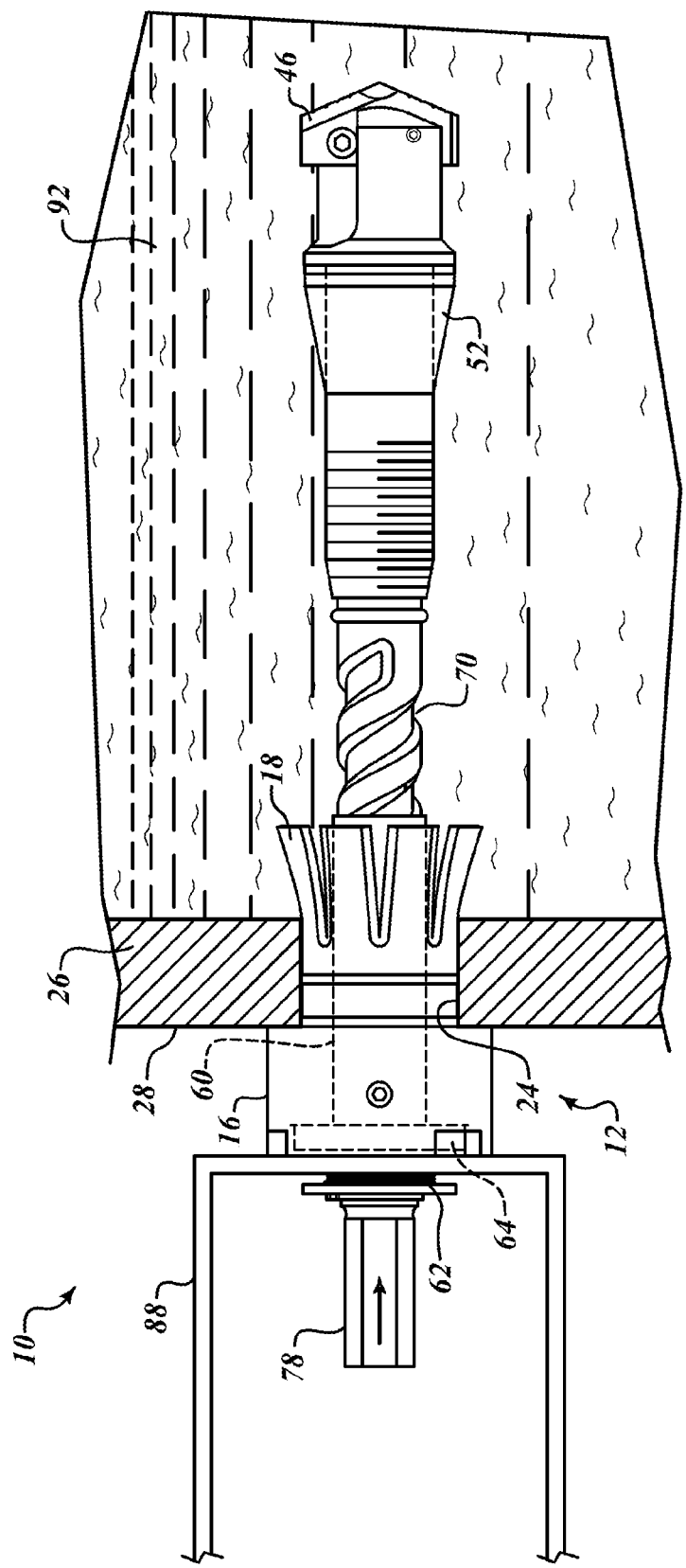
FIG. 10 is a side elevational view of the sample retrieval tool showing the multi-section tool bit moved further forward to extend into an interior of the structure or workpiece with a cover or sleeve of the sample chamber open, exposing an auger section of the multi-section tool bit, according to one illustrated embodiment.

FIG. 10 shows the sample retrieval tool 10 with the sample chamber 47 open and an auger portion 70 of the multi-section tool bit 14 exposed on interior or blind side 94 of the workpiece 26. In particular, the machine 80 may rotate the multi-section tool bit 14, for instance in the first rotational direction (e.g., clockwise) to cause the auger portion 70 to rotate and acquire a sample of the material 92 in the sample chamber 47. Such may be particularly advantageous for sampling viscous or extremely viscous fluids, for instance oil at the low temperatures associated with deep water. Notably, in some instances the interior or blind side 94 of the workpiece 26 may be empty and no material is collected or a material 92 held by the workpiece 26 may be positioned such that the material 92 cannot be reached by the sample chamber 47 from the hole 24 and no material is collected. However, even in such circumstances, the sample retrieval may be considered successful, indicating that no material is present within the workpiece 26 at a give location.

Figure 11:
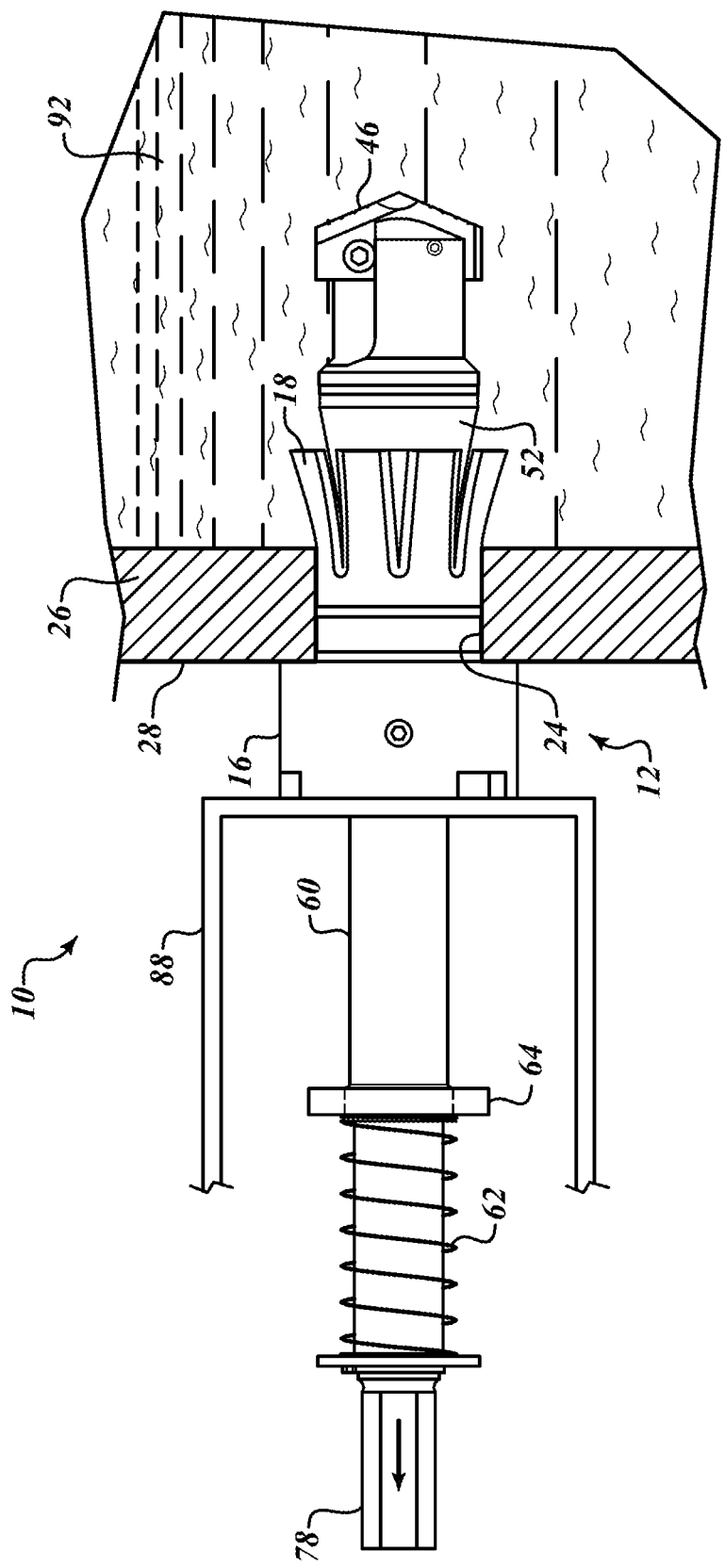
FIG. 11 is a side elevational view of the sample retrieval tool showing the multi-section tool bit moved rearwardly with the cover or sleeve of the sample chamber in a closed position and the mandrel section positioned to engage the body of the plug, according to one illustrated embodiment.

FIG. 11 shows the sample retrieval tool 10 with the multi-section tool bit 14 moved rearwardly with respect to the plug 12 and workpiece 26 to close the sample chamber 47 and retain the sample therein. In particular, a force may be applied by the machine 80 or gripper or holder 88 to translate the multi-section tool bit 14 outwardly from the structure or workpiece 26. The plug 12 is fixed in the workpiece 26 so does not translate along with the multi-section tool bit 14. The cover or sleeve 60 of the sample chamber 47 may be biased forwardly, for example by compression spring 62, back to a normally closed position. The cover or sleeve 60 may engage the sleeve stop 68 when in the closed position.

Figure 12:
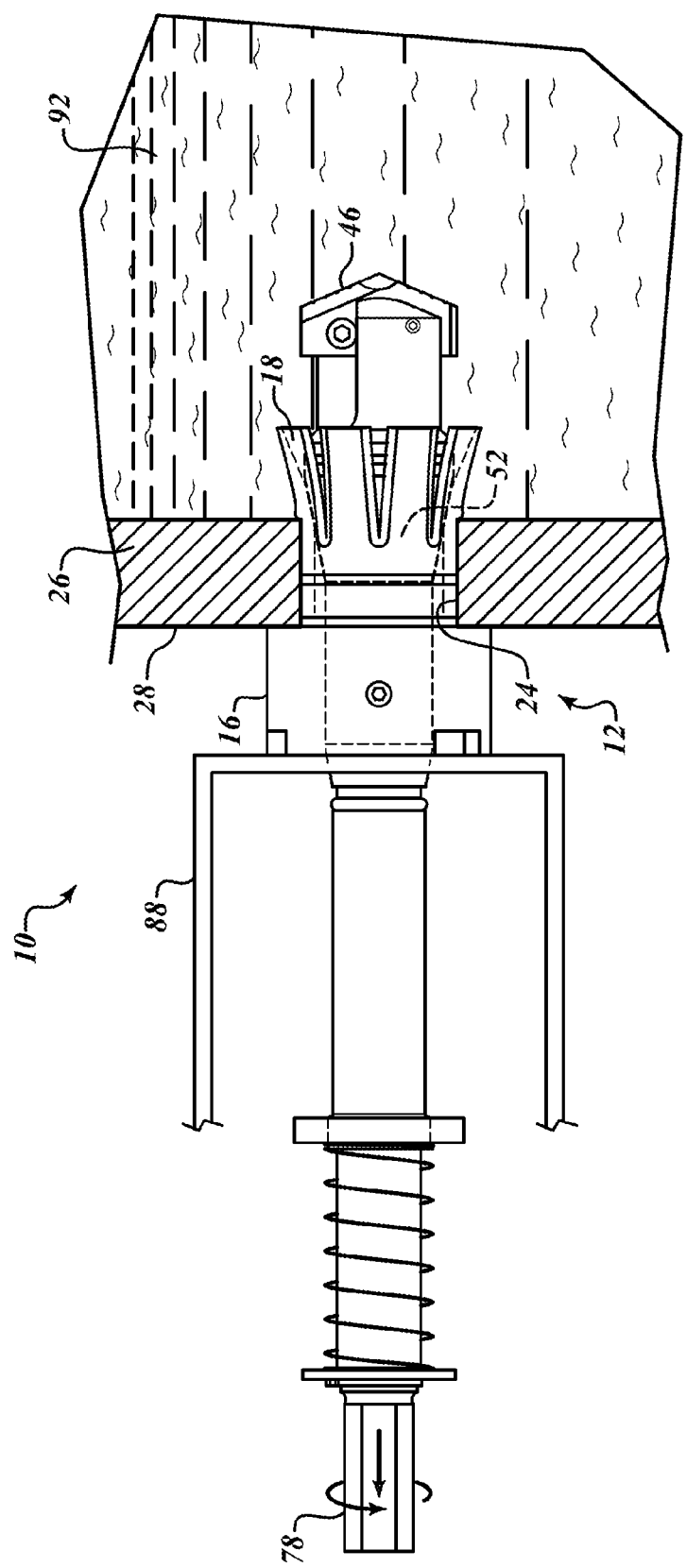
FIG. 12 is a side elevational view of the sample retrieval tool showing the mandrel section of the multi-section tool bit moved further rearwardly in the passage of the plug to sealing the plug, according to one illustrated embodiment.

FIG. 12 shows the sample retrieval tool 10 with mandrel section 52 of the leading section 42 of the multi-section tool bit 14 securely seated in the passage 20 of the body 18 of the plug 12. Such effectively closes the passage 20 and secures the plug 12 against leakage. In particular, the machine 80 (FIG. 4) may rotate the multi-section tool bit 14, for example in the second rotational direction (e.g., counterclockwise) to move the leading section 42 and mandrel section rearwardly into the passage 20. Rotation may cause the externally threaded portion 36 to engage or reengage the thread passage 34 of the nut 32 of the plug 12.

Figure 13:
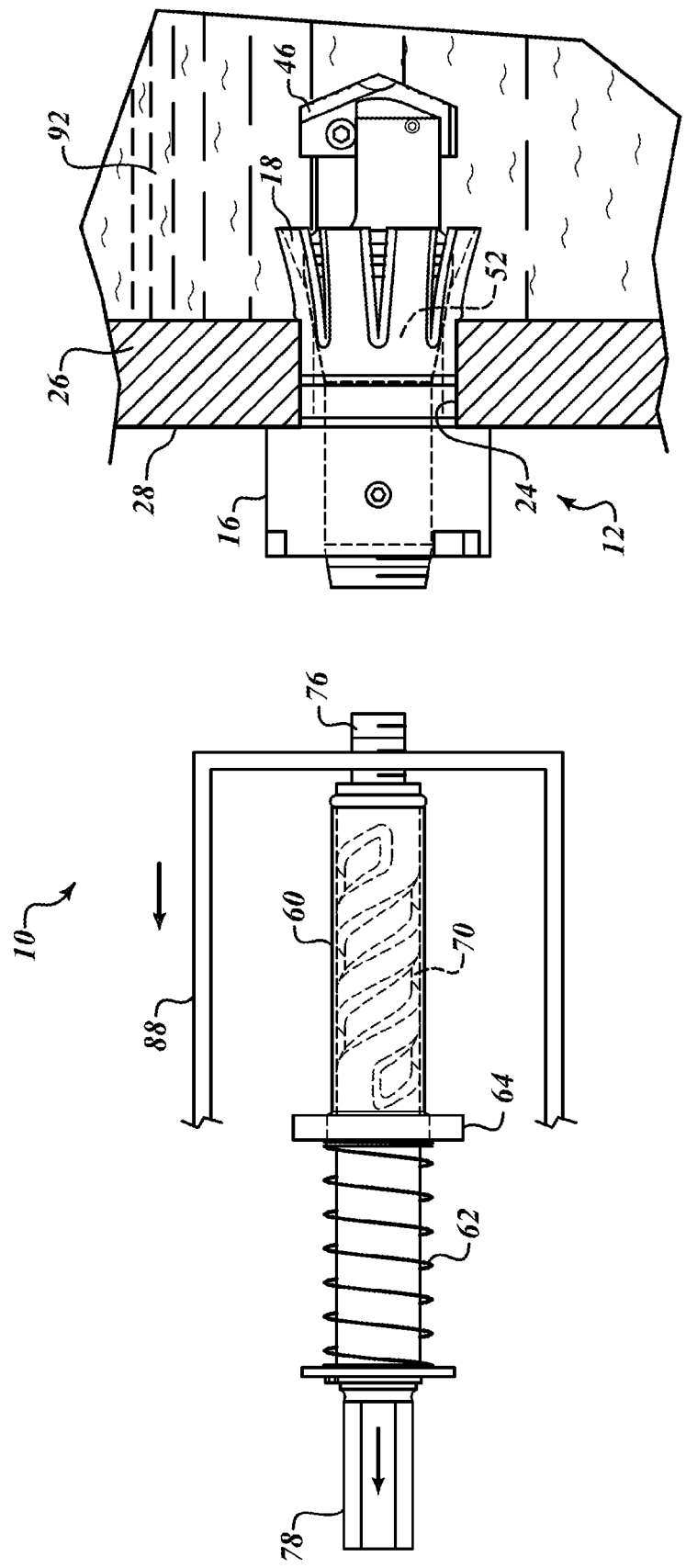
FIG. 13 is a side elevational view of the sample retrieval tool showing the trailing section of the multi-section tool bit including the sample chamber detached from the leading section of the multi-section tool bit including the cutter and mandrel section, according to one illustrated embodiment.

FIG. 13 shows the sample retrieval tool 10 with the trailing section 44 of the multi-section tool bit 14 separated from the leading section 42 of the multi-section tool bit 14. The trailing section 44 includes the sample chamber 47, so may be returned to a desired location (e.g., surface) to examine the sample. The leading section 42 of the multi-section tool bit 14 remains secured in the passage 20 of the plug 12, preventing leakage through the hole 24 from the interior or blind side 94 of the workpiece 26. In particular, the machine 80 may rotate the multi-section tool bit 14, for example in the second rotational direction (e.g., counterclockwise) to unthread or unscrew the trailing section 44 from the leading section 42. Alternatively, the machine 80 may rotate to apply a torque to the multi-section tool bit 14 sufficient to cause shearing at the separate section or feature (e.g., necked region) between the leading and trailing sections 42, 44.

Figure 14:
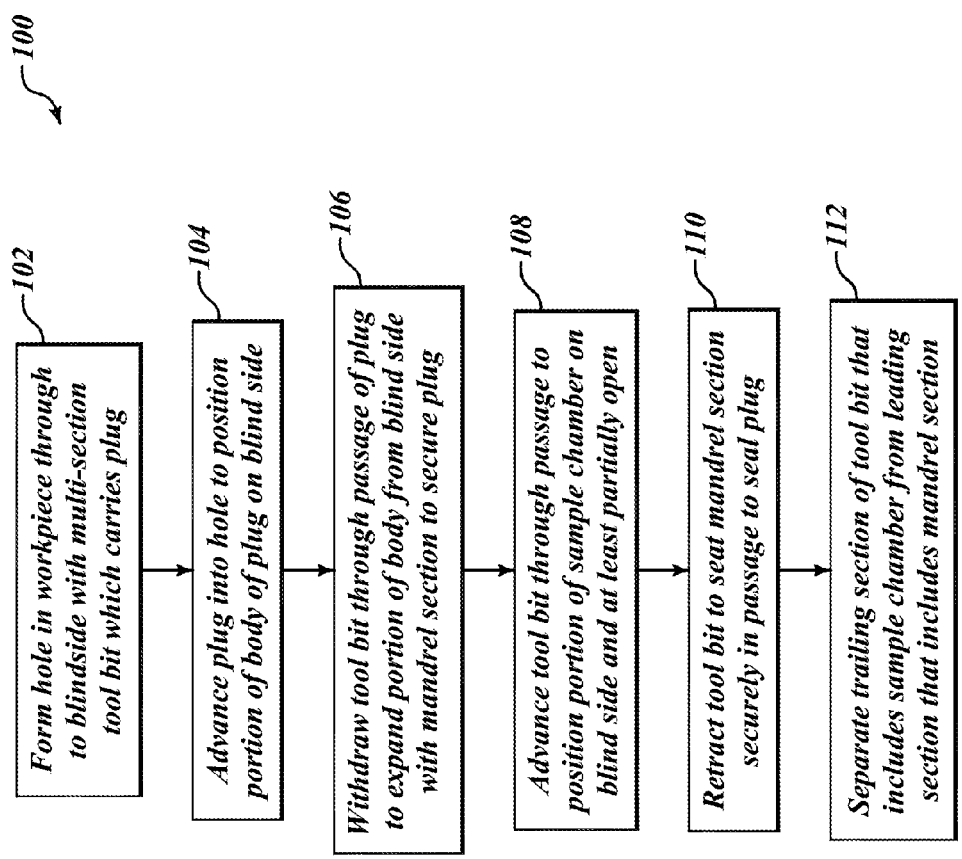
FIG. 14 is a flow diagram showing a method of operating a sample retrieval tool to form a hole in a structure, retrieve samples from an interior of the structure, and perform a blind side expansion to seal the hole in the structure, according to one illustrated embodiment.

FIG. 14 shows a method 100 of operating a sample retrieval tool 10, according to one illustrated embodiment.

At 102, the cutter 46 of the multi-section tool bit 14 forms a hole 24 in the workpiece 26 from a front side through to a blind side of the workpiece 26. The multi-section tool bit 14 carries the plug 12. A machine 80 or other actuator may rotate or otherwise move (e.g., hammer drill) the cutter to form the hole 24.

At 104, the plug 12 is advanced into the formed hole 24 to position a portion of a body 18 of the plug 12 in the blind side of the workpiece 26. Such may be done by engaging a portion of the plug 12 (e.g., head 16) with a portion of the multi-section tool bit 14. Alternatively or additional, such may be accomplished by translating the gripper or holder 88 which contacts a portion of the plug 12.

At 106, the multi-section tool bit 14 is partially withdrawn through the passage 20 in the plug 12 to expand at least a portion of the body 18 of the plug 12 from the blind side 94 of the workpiece 26 with a mandrel section 52 of the multi-section tool bit 14. This secures the plug 12 in the hole 24 formed with the cutter 46. The multi-section tool bit 14 may be partially withdrawn by rotating the multi-section tool bit 14 with the machine 80. Threaded engagement between the externally threaded portion 36 and the threaded passage 34 of the nut 32 of the plug 12 may cause the desired translation in response to the rotation. The externally threaded portion 36 and the threaded passage 34 of the nut 32 may become disengaged during this act, allowing translation of the remainder of the multi-section tool bit 14.

At 108, the multi-section tool bit 14 is advanced through the passage 20 in the plug 12 to position at least a portion of a sample chamber 47 of the multi-section tool bit 14 on the blind side 94 of the workpiece 26 with the sample chamber 47 at least partially open. Such may be accomplished by translating the multi-section tool bit 14.

At 110, the multi-section tool bit 14 is retracted rearwardly to seat the mandrel section 52 of the multi-section tool bit 14 securely in a portion of the passage 20 that extends through at least a portion of the body 18 of the plug 12. Such seals the plug 12 from leakage. The multi-section tool bit 14 may be retracted by rotating the multi-section tool bit 14 with the machine 80. The externally threaded portion 36 and the threaded passage 34 of the nut 32 of the plug 12 threadedly reengage and cause the desired translation in response to the rotation.

At 112, a trailing portion of the multi-section tool bit 14 that includes the sample chamber 47 is separated from a leading portion of the multi-section tool bit 14 that includes the mandrel section 52. This allows the trailing portion 44 to be retrieved and brought to a suitable location to examine or analyze the sample. In some instances, this may mean returning the sample chamber 47 with the sample to a surface ship or other facility. In other instances, this may mean locating the sample in a suitable vessel, for example underwater, and examining such with one or more cameras or suitable analytic equipment.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other sample retrieval apparatus and methods, not necessarily the exemplary sample retrieval apparatus and methods generally described above. For example, to retrieval tool may be employed on vehicle other than ROVs or submersible ROVs, or may even be operated manually by hand.

For example, the cutter 46 can take any variety of types of drills, millers, borers, reamers or other cutters which are suitable for the particular workpiece and/or work environment. For instance and without limitation, the cutter 46 may take the form of a spade drill, fluted mill, straight shank drills such as common twist drills (e.g., high or low helix drills, screw machine drills), straight fluted drills, three- and four-fluted drills parabolic fluted drills, half round drills or hole saw. Applicants believe that a spade drill may be preferable to other types of cutters. The cutter 46 and/or the stem 48 and/or the shank 56 may be formed from a variety of materials suitable for the particular workpiece 20 and application. Typically material may include high carbon steel, titanium alloy, high speed steel, cobalt steel, and tungsten carbide steel. The cutter 46 and/or possible the stem 48 and/or the shank 56 may carry a coating, for example a black oxide, titanium nitride, titanium aluminum nitride, titanium carbon nitride, diamond powder or zirconium nitride. Notably, when the intended application is underwater, lubricant may not be a consideration, although the possibility of corrosion may be a concern, particularly in salt water.

Also for example, the machine 80 may take any of a variety of forms, for instance rotary drill, hammer drill, rotary hammer drill, milling machine or reamer machine.

Also for example, the sample chamber 47 can take a different form and/or employ a different mechanism to open and close such. For instance, instead of a sliding cover or sleeve 60, the sample chamber 47 may employ a flap or flip top, which may be hinged, for example at an forward end of the sample chamber 47. Alternatively, the cover or sleeve may be threaded to translate in response to rotation thereof relative to some other portion such as the leading section 42. Further, the sample chamber may employ any variety of biasing member, not necessarily the illustrated coil compression spring. For example, other springs may be employed, for instance leaf springs. Also for example, a resilient material may be employed or a shape memory material such as a shape memory alloy (e.g., Nitinol) may be employed.

Also for example, the multi-section drill bit 14 may have more than two separable sections.

The various embodiments described above can be combined to provide further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A sample retrieval tool to form a hole in a workpiece, retrieve samples from an interior of the workpiece and to perform a blind side expansion to seal the hole in the workpiece, the sample retrieval tool comprising:
a plug comprising a head and a body, a flange bearing surface formed by a transition between the head and the body to bear against an exterior surface of the workpiece, a passage extending through the head and the body, the body being plastically expandable between an unexpanded configuration in which a portion of the body is sized to be receivable through the hole in the workpiece and an expanded configuration in which at least some of the portion of the body is sized to be in sealing engagement with at least a portion of the workpiece; and
a multi-section tool bit comprising a leading section and a trailing section selectively detachable from the leading section, the leading section comprising an elongated stem having a front end and a rear end, a cutter at least proximate at least the front end of the stem, a mandrel section spaced rearwardly from the cutter, the mandrel section having an outer perimeter sized to be received in a portion of the passage that extends through the body of the plug and to plastically expand at least a portion of the body of the plug into the expanded configuration as the mandrel section is moved rearwardly through the portion of the passage from a blindside of the hole in the workpiece, the trailing section comprising an elongated shank having a leading end, a trailing end, and a sample chamber that is openable to receive a sample therein and closable to retain the sample therein.

2. The sample retrieval tool of claim 1 wherein the trailing section of the tool bit includes an auger portion.

3. The sample retrieval tool of claim 1 wherein the sample chamber is formed by a sleeve that surrounds a portion of trailing section of the tool bit.

4. The sample retrieval tool of claim 3 wherein the sleeve is selectively displaceable from a closed position in which the sample chamber is open to receive the sample to a closed position in which the sample chamber is closed to retain the sample therein.

5. The sample retrieval tool of claim 4 wherein the trailing section of the tool bit includes a spring that biases the sleeve toward the closed position.

6. The sample retrieval tool of claim 4 wherein the trailing section of the tool bit includes a sleeve stop extending radially from the shank of the trailing section and the trailing section also includes a spring that biases the sleeve forwardly toward the closed position in which a portion of the sleeve engages the sleeve stop.

7. The sample retrieval tool of claim 1 wherein the stem of the leading section of the tool bit has an externally threaded portion rearward of the cutter, the body and the head of the plug are a unitary piece of a plastic material, and the plug further comprises a metal nut received in the passage in the head and having a threaded passage sized to threadedly receive the externally threaded portion of the leading section of the tool bit.

8. The sample retrieval tool of claim 7 wherein the passage is longitudinal, the body has a number of longitudinally extending flutes formed therein and a number of seals thereabout, and the metal nut is retained in the longitudinal passage in the head by a number of set screws.

9. The sample retrieval tool of claim 7 wherein at least a portion of the passage of the plug is tapered, having an inner perimeter that decreases in size along a longitudinal axis in a direction towards the head of the plug.

10. The sample retrieval tool of claim 1 wherein the leading and trailing sections of the tool bit have a separable portion therebetween that allows the separation of the leading section from the trailing section.

11. The sample retrieval tool of claim 10 wherein the leading section is attachably and detachably coupled to the trailing section by the separable portion.

12. The sample retrieval tool of claim 10 wherein the separable portion includes a leading section coupler at least proximate the rear end of the stem and the trailing section coupler at least proximate a leading end of the shank that is complimentary to the leading section coupler.

13. The sample retrieval tool of claim 12 wherein the leading section of the tool bit has an externally threaded portion rearward of the cutter, the leading section coupler includes a threaded female member and the coupler of the trailing section includes a threaded male member threadably engageable with the threaded female member of the leading section, and a thread of the externally threaded portion is reverse with respect to a thread of the threaded female member.

14. The sample retrieval tool of claim 1 wherein the leading and trailing sections of the tool bit have a necked region therebetween, the necked region sized to break to separate the leading section from the trailing section under a defined torque.

15. The sample retrieval tool of claim 1 wherein the mandrel section is a tapered mandrel section having an outer perimeter that decreases rearwardly along the tapered mandrel section.

16. The sample retrieval tool of claim 15 wherein the tapered mandrel section is slidably receivable on the stem, and the leading section further comprises a washer received on the stem between the tapered mandrel and the cutter.

17. The sample retrieval tool of claim 1 wherein the trailing section has a coupler at least proximate the trailing end; and further comprising:
a drill comprising a motor and a coupler sized and dimension to drivingly couple to the coupler of the trailing section of the tool bit; and
a grip selectively operable to engage the head of the plug and to push the body of the plug into the hole in the workpiece.

18. The sample retrieval tool of claim 1 wherein the trailing section has a coupler at least proximate the trailing end; and further comprising:
a drill comprising a motor and a coupler sized and dimension to drivingly couple to the coupler of the trailing section of the tool bit; and
a grip selectively operable to engage the head of the plug and prevent rotation of the plug in the hole in the workpiece.

19. A method of operating a sample retrieval tool including a plug and multi-section tool bit to retrieve a sample from an interior of a workpiece, the method comprising:

forming a hole in the workpiece from one side through to a blindside of the workpiece with the multi-section tool bit while the tool bit carries the plug;

advancing the plug into the formed hole to position a portion of a body of the plug in the blind side of the workpiece;

withdrawing the tool bit through a passage in the plug to expand at least a portion of the body of the plug from the blind side of the workpiece with a mandrel section of the tool bit to secure the plug in the hole;

advancing the tool bit through the passage in the plug to position at least a portion of a sample chamber of the tool bit on the blind side of the workpiece with the sample chamber at least partially open;

retracting the tool bit to seat the mandrel section of the tool bit securely in a portion of the passage that extends through at least a portion of the body of the plug; and separating a portion of the tool bit that includes the sample chamber from a portion of the tool bit that includes the mandrel section.

20. The method of claim 19 wherein forming a hole in the workpiece includes rotating the tool bit in a first rotational direction and wherein withdrawing the tool bit through a passage in the plug includes rotating the tool bit in a second rotational direction, opposite the first rotational direction.

21. The method of claim 20 wherein advancing the tool bit through the passage in the plug to position at least a portion of a sample chamber of the tool bit on the blind side of the workpiece includes rotating the tool bit in the first rotational direction.

22. The method of claim 21 wherein separating a portion of the tool bit that includes the sample chamber from a portion of the tool bit that includes the mandrel section includes rotating the tool bit in the second rotational direction to apply a torque to the tool bit after the mandrel section has securely engaged the plug in the hole in the workpiece.

23. The method of claim 19, further comprising:

pulling the tool bit rearwardly to close the sample chamber; and reengaging a thread on the tool bit with a thread of the plug after pulling the tool bit rearwardly and before retracting the tool bit.

24. The method of claim 19, further comprising:

rotating the tool bit to auger a viscous fluid into the sample chamber after advancing the tool bit through the passage in the plug to position at least a portion of a sample chamber of the tool bit on the blind side of the workpiece and before retracting the tool bit.

25. The method of claim 19 wherein withdrawing the tool bit through a passage in the plug to expand at least a portion of the body of the plug from the blind side of the workpiece with a mandrel section of the tool bit to secure the plug in the hole includes withdrawing the tool bit through the passage to expand at least the portion of the body of the plug from the blind side of the workpiece with a tapered mandrel section of the tool bit.

26. The method of claim 19 wherein advancing the plug into the formed hole to position a portion of a body of the plug in the blind side of the workpiece includes pushing the plug with a holder.

27. A plug for use in sample retrieval to seal a hole in a workpiece via a blind side expansion of a portion of the plug while allowing retrieval of a sample from with the workpiece, the plug comprising:

a unitary piece of a plastic material having a head, a body and a flange bearing surface formed by a transition between the head and the body to bear against an exterior surface of the workpiece, a passage extending through the head and the body, the body having a number of longitudinally extending flutes formed therein, at least a portion of the body being plastically expandable between an unexpanded configuration in which a portion of the body is sized receivable through the hole in the workpiece and an expanded configuration in which at least some of the portion of the body is sized to be in sealing engagement with at least a portion of the workpiece when expanded from the blind side of the workpiece by a mandrel pull through the passage of the plug; and a metal nut that is retained in the passage in the head.

28. The plug of claim 27 wherein the body is a cylindrical tube and the passage is longitudinal.

29. The plug of claim 27, further comprising:

at least two O-ring seals received about an exterior of the body and spaced longitudinally along the body with respect to one another.

30. The plug of claim 27, further comprising:

a number of set screws that retain the metal nut in the passage in the head.

31. The plug of claim 27 wherein at least a portion of the passage is tapered, having an inner perimeter that decreases in size along a longitudinal axis in a direction towards the head of the plug.

* * * * *